United States Patent
Tamai et al.

(10) Patent No.: US 6,353,025 B1
(45) Date of Patent: Mar. 5, 2002

(54) PHENYLAMINOALKYLCARBOXYLIC ACID DERIVATIVES AND PHARMACEUTICAL COMPOSITIONS COMPRISING THE SAME

(75) Inventors: Tetsuro Tamai; Nobuyuki Tanaka; Harunobu Mukaiyama; Akihito Hirabayashi; Hideyuki Muranaka; Masaaki Sato; Masuo Akahane, all of Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/581,851
(22) PCT Filed: Dec. 11, 1998
(86) PCT No.: PCT/JP98/05605
§ 371 Date: Jun. 19, 2000
§ 102(e) Date: Jun. 19, 2000
(87) PCT Pub. No.: WO99/31045
PCT Pub. Date: Jun. 24, 1999

(30) Foreign Application Priority Data

Dec. 18, 1997 (JP) ............................................. 9-370087

(51) Int. Cl.$^7$ ..................... A01N 37/12; A01N 37/44; A61K 31/24
(52) U.S. Cl. ..................... 514/539; 560/37; 560/39; 562/451
(58) Field of Search .............................. 560/43, 37, 39; 514/539, 784; 562/451

(56) References Cited

U.S. PATENT DOCUMENTS

| | | | |
|---|---|---|---|
| 4,146,638 A | * | 3/1979 | Renth .......................... 424/304 |
| 4,629,737 A | | 12/1986 | Cantello |
| 5,153,210 A | | 10/1992 | Ainsworth et al. |

FOREIGN PATENT DOCUMENTS

EP 0 068 669 A1 6/1982

* cited by examiner

Primary Examiner—Gary Geist
Assistant Examiner—Zachary C. Tucker
(74) Attorney, Agent, or Firm—Sughrue, Mion, Zinn, Macpeak & Seas, PLLC

(57) ABSTRACT

The present invention provides novel phenylaminoalkyl-carboxylic acid derivatives represented by the general formula:

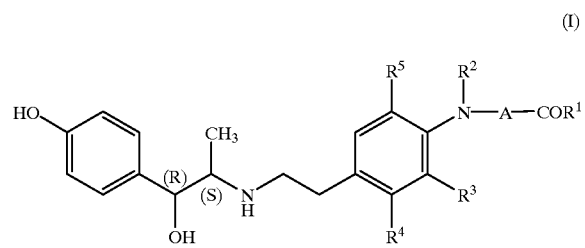

(I)

(wherein $R^1$ represents a hydroxy group, a lower alkoxy group, an aralkoxy group, an amino group, an alicyclic amino group or a mono or di(lower alkyl)amino group which may have a hydroxy group or a lower alkoxy group as a substituent; $R^2$ represents a hydrogen atom or a lower alkyl group; $R^3$ represents a hydrogen atom or a halogen atom; $R^4$ and $R^5$ are the same or different and each represents a hydrogen atom, a halogen atom or a lower alkyl group; A represents a lower alkylene group; the carbon atom marked with (R) represents a carbon atom in (R) configuration; and the carbon atom marked with (S) represents a carbon atom in (S) configuration) and pharmaceutically acceptable salts thereof, which have excellent $\beta_3$-adrenoceptor stimulating effects and are useful as agents for the prevention or treatment of obesity, hyperglycemia, the diseases caused by intestinal hypermotility, pollakiuria, urinary incontinence, depression, or the diseases caused by biliary calculi or hypermotility of biliary tract.

9 Claims, No Drawings

PHENYLAMINOALKYLCARBOXYLIC ACID DERIVATIVES AND PHARMACEUTICAL COMPOSITIONS COMPRISING THE SAME

TECHNICAL FIELD

The present invention relates to novel phenylaminoalkylcarboxylic acid derivatives and pharmaceutically acceptable salts thereof which are useful as medicaments.

BACKGROUND ART

It is known that three subtypes of sympathomimetic β-adrenoceptors, which have been classified as $\beta_1$, $\beta_2$ and $\beta_3$, are present and that each receptor subtype is distributed in specified organs in the living body and has specific functions.

For example, $\beta_1$-adrenoceptor is mainly present in the heart and the stimulation of this receptor leads to increase of heart rate and cardiac contractility. $\beta_2$-Adrenoceptor is mainly present in smooth muscle of blood vessels, the trachea and uterus. The stimulation of this receptor leads to vasodilation, bronchodilation and inhibition of uterine contraction. $\beta_3$-Adrenoceptor is mainly present in adipocytes, the gall bladder and intestinal tract. It is known that $\beta_3$-adrenoceptor is also present in the brain, liver, prostate and stomach. It has been reported that the stimulation of $\beta_3$-adrenoceptor leads to increase of lipolysis, inhibition of intestinal tract motility, increase of glucose uptake, antidepression and so on (Drugs of the Future, Vol.18, No.6, pp. 529–549 (1993); Molecular Brain Research, Vol.29, pp.369–375 (1995); European Journal of Pharmacology, Vol.289, pp.223–228 (1995); Pharmacology, Vol.51, pp.288–297 (1995)).

In addition, it has been recently reported that $\beta_3$-adrenoceptor is predominantly present in the human bladder and that the human bladder is relaxed by a $\beta_3$-adrenoceptor stimulant (The Japanese Journal of Urology, Vol.88, No.2, p.183 (1997); NEUROUROLOGY AND URODYNAMICS, Vol.16, No.5, pp.363–365 (1997)).

Many $\beta_1$-adrenoceptor stimulants and $\beta_2$-adrenoceptor stimulants have been developed and are used for medicinal purposes as cardiotonics, bronchodilators, preventive agents for threatened abortion or premature labor, and so on.

On the one hand, it has been found that $\beta_3$-adrenoceptor stimulants are useful as agents for the prevention or treatment of obesity, hyperglycemia, the diseases caused by intestinal hypermotility, pollakyuria, urinary incontinence, depression, the diseases caused by biliary calculi or hypermotility of the biliary tract (hereafter simply "biliary tract") and so on. Consequently, studies have been actively made to develop agents for the prevention or treatment of such diseases, but no $\beta_3$-adrenoceptor stimulant has been sold yet (Drugs of the Future, Vol.18, No.6, pp.529–549(1993); European Journal of Pharmacology, Vol.219, pp.193–201 (1992) etc.).

Therefore, it has been desired to develop novel $\beta_3$-adrenoceptor stimulants having excellent $\beta_3$-adrenoceptor stimulating effects.

More preferably, it has been desired to develop novel and higher selective $\beta_3$-adrenoceptor stimulants having potent $\beta_3$-adrenoceptor stimulating effects in comparison with $\beta_1$ and/or $\beta_2$-adrenoceptor stimulating effects and having attenuated side effects aused by $\beta_1$ and $\beta_2$-adrenoceptor stimulating effects such as alpitation and tremor.

DISCLOSURE OF THE INVENTION

The present inventors have studied extensively to meet the above objects. As a result, it was found that certain phenylaminoalkylcarboxylic acid derivatives have potent stimulating effects on β3-adrenoceptors, thereby forming the basis of the present invention.

Accordingly, the present invention relates to a phenylaminoalkylcarboxylic acid derivative represented by the general formula:

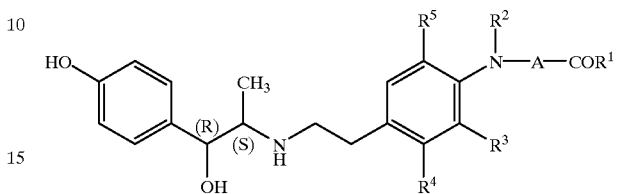

(I)

(wherein $R^1$ represents a hydroxy group, a lower alkoxy group, an aralkoxy group, an amino group, an alicyclic amino group or a mono or di(lower alkyl)amino group which may have a hydroxy group or a lower alkoxy group as a substituent; $R^2$ represents a hydrogen atom or a lower alkyl group; $R^3$ represents a hydrogen atom or a halogen atom; $R^4$ and $R^5$ are the same or different and each represents a hydrogen atom, a halogen atom or a lower alkyl group; A represents a lower alkylene group; the carbon atom marked with (R) represents a carbon atom in (R) configuration; and the carbon atom marked with (S) represents a carbon atom in (S) configuration) or a pharmaceutically acceptable salt thereof.

The present invention relates to a pharmaceutical composition comprising the phenylaminoalkylcarboxylic acid derivative represented by the above general formula (I) or a pharmaceutically acceptable salt thereof.

The present invention relates to a $\beta_3$-adrenoceptor stimulant comprising as the active ingredient the phenylaminoalkylcarboxylic acid derivative represented by the above general formula (I) or a pharmaceutically acceptable salt thereof.

The present invention relates to an agent for the prevention or treatment of obesity, hyperglycemia, the diseases caused by intestinal hypermotility, pollakiuria, urinary incontinence, depression, or the diseases caused by biliary calculi or hypermotility of biliary tract which comprises as the active ingredient the phenylaminoalkylcarboxylic acid derivative represented by the above general formula (I) or a pharmaceutically acceptable salt thereof.

The present invention relates to a method for the prevention or treatment of obesity, hyperglycemia, the diseases caused by intestinal hypermotility, pollakiuria, urinary incontinence, depression, or the diseases caused by biliary calculi or hypermotility of biliary tract which comprises administrating a therapeutically effective amount of the phenylaminoalkylcarboxylic acid derivative represented by the above general formula (I) or a pharmaceutically acceptable salt thereof.

The present invention relates to a use of the phenylaminoalkylcarboxylic acid derivative represented by the above general formula (I) or a pharmaceutically acceptable salt thereof for the manufacture of a pharmaceutical composition for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a use of the phenylaminoalkylcarboxylic acid derivative represented by the above general formula (I) or a pharmaceutically acceptable salt thereof as an agent for the prevention or treatment of obesity, hyperglycemia, the diseases caused by intestinal hypermotility, pollakiuria, urinary incontinence, depression, or the diseases caused by biliary calculi or hypermotility of biliary tract.

The present invention relates to a process for the manufacture of a pharmaceutical composition for the prevention or treatment of obesity, hyperglycemia, the diseases caused by intestinal hypermotility, pollakiuria, urinary incontinence, depression, or the diseases caused by biliary calculi or hypermotility of biliary tract, characterized in the use, as an essential constituent of said pharmaceutical composition, of the phenylaminoalkylcarboxylic acid derivative represented by the above general formula (I) or a pharmaceutically acceptable salt.

In the compounds represented by the above general formula (I) of the present invention, the term "lower alkoxy group" means a straight or branched alkoxy group having 1 to 6 carbon atoms such as a methoxy group, an ethoxy group, a propoxy group, an isopropoxy group and a butoxy group; the term "aralkoxy group" means the above lower alkoxy group having an aryl group such as a phenyl group and a naphthyl group; the term "lower alkyl group" means a straight or branched alkyl group having 1 to 6 carbon atoms such as a methyl group, an ethyl group, a propyl group, an isopropyl group and a butyl group; the term "alicyclic amino group" means an aliphatic cycloamino group which may have an oxygen atom in the ring chain such as a piperidino group, a morpholino group and a 1-pyrrolidinyl group; the term "halogen atom" means a fluorine atom, a chlorine atom, a bromine atom or an iodine atom; and the term "lower alkylene group" means a straight alkylene group having 1 to 6 carbon atoms such as a methylene group, an ethylene group, a trimethylene group and a tetramethylene group.

The compounds represented by the above general formula (I) of the present invention can be prepared according to the following procedures.

For example, the compounds of the present invention can be prepared by allowing an amine compound represented by the formula:

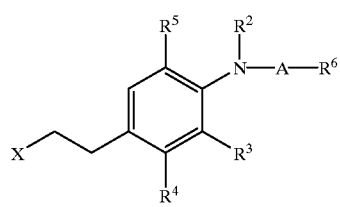

(II)

(wherein the carbon atom marked with (R) and the carbon atom marked with (S) have the same meanings as defined above) to react with an alkylating agent represented by the general formula:

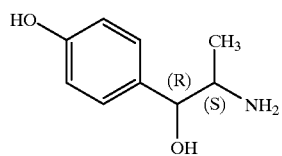

(III)

(wherein $R^6$ represents a protected carboxy group; X represents a leaving group; and $R^2$, $R^3$, $R^4$, $R^5$ and A have the same meanings as defined above) in the presence or absence of a base such as N,N-diisopropylethylamine in an inert solvent such as N,N-dimethyl-formamide, removing the carboxy-protective group or subjecting the resulting compound to amidation using ammonia, a mono or di (lower alkyl) amine compound which may have a hydroxy group or a lower alkoxy group as a substituent, or an alicyclic amine compound in the usual way as occasion demands.

The amine compound represented by the above formula (II) which is used as a starting material in the above production process can be prepared by optical resolution of a commercially available enantiomeric mixture in the usual way or a method described in the literature (e.g., J. Med. Chem., Vol. 20, No. 7, pp.978–981(1977)).

The compounds represented by the above general formula (III) which are used as starting materials in the above production process can be prepared by subjecting an amine compound represented by the general formula:

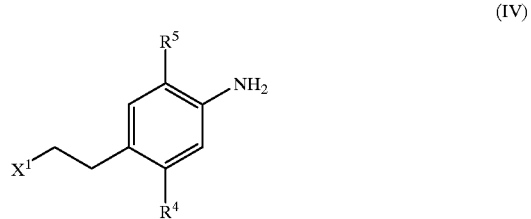

(IV)

(wherein $X^1$ represents a hydroxy group, a chlorine atom or a bromine atom; and $R^4$ and $R^5$ have the same meanings as defined above) to N-alkylation using an alkylating agent represented by the general formula:

$$X^2—A—R^6 \qquad (V)$$

(wherein $X^2$ represents a chlorine atom, a bromine atom or an iodine atom; and $R^6$ and A have the same meanings as defined above) in the presence of a base such as potassium carbonate, subjecting the resulting compound to halogenation of the benzene ring and/or alkylation of the secondary amino group in the usual way as occasion demands to give a compound represented by the general formula:

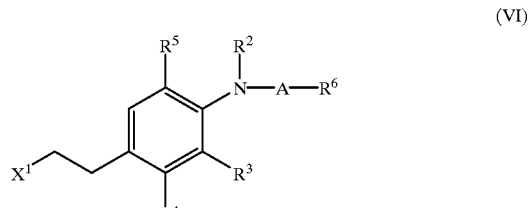

(VI)

(wherein $R^2$, $R^3$, $R^4$, $R^5$, $R^6$, A and $X^1$ have the same meanings as defined above), and, when $X^1$ is a hydroxy group, converting the hydroxy group to a leaving group in the usual way.

Of the compounds represented by the above general formula (III) which are used as starting materials in the above production process, compounds represented by the general formula:

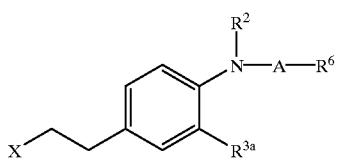
(IIIa)

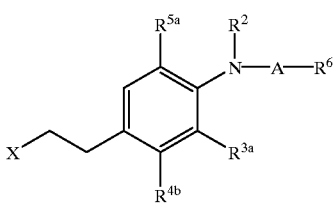
(IIIb)

(wherein $R^{3a}$ represents a halogen atom; and $R^2$, $R^6$, A and X have the same meanings as defined above) can be prepared by subjecting a phenethyl alcohol derivative represented by the general formula:

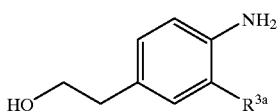
(VII)

(wherein $R^{3a}$ has the same meaning as defined above) to protection of the amino group and the hydroxy group by a trifluoroacetyl group and a tetrahydropyranyl group respectively in the usual way, subjecting the resulting compound represented by the general formula:

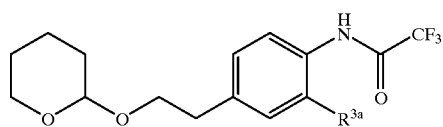
(VIII)

(wherein $R^{3a}$ has the same meaning as defined above) to N-alkylation using the alkylating agent represented by the above general formula (V) in the presence of a base such as sodium hydride, removing the protective group of the amino group and the hydroxy group, subjecting the resulting compound to alkylation of the secondary amino group in the usual way as occasion demands to give a compound represented by the general formula:

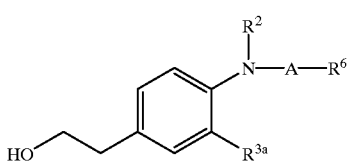
(IX)

(wherein $R^2$, $R^{3a}$, $R^6$ and A have the same meanings as defined above) and converting the hydroxy group to a leaving group in the usual way.

Of the compounds represented by the above general formula (III) which are used as starting materials in the above production process, compounds represented by the general formula:

(wherein $R^{4b}$ represents a halogen atom; $R^{5a}$ represents a hydrogen atom or a halogen atom; and $R^2$, $R^3$, $R^6$, A and X have the same meanings as defined above) can be prepared by converting the hydroxy group of a phenethyl alcohol derivative represented by the general formula:

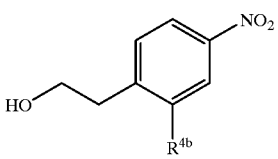
(X)

(wherein $R^{4b}$ has the same meaning as defined above) to a leaving group in the usual way, reducing the nitro group to an amino group in the usual way, subjecting the resulting compound to N-alkylation using the alkylating agent represented by the above general formula (V) in the presence of a base such as potassium carbonate to give a compound represented by the general formula:

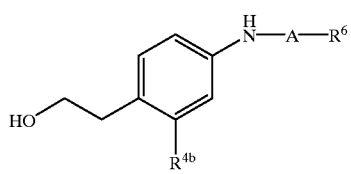
(XI)

(wherein $R^{4b}$, $R^6$, A and X have the same meanings as defined above) and subjecting the resulting compound to halogenation of the benzene ring and/or N-alkylation of the secondary amino group in the usual way as occasion demands.

The compounds represented by the above general formulae (IV), (V), (VII) and (X) which are used as starting materials in the above production process can be prepared from a commercially available reagent in the usual way or a method described in the literature (Org. Synth., III, pp.183–184(1955); J. Med. Chem., Vol.15, No.5, pp. 490–493(1972); a published Japanese Patent Application (KOKOKU) No. Sho 47-45747; J. Med. Chem., Vol.28, No.12, pp.1828–1832(1985); Helvetica Chimica Acta, Vol.64, pp.1688–1703(1981) etc.).

In the above production process, the term "protected carboxy group" means an ester group including a straight or branched alkoxy group having 1 to 6 carbon atoms such as a methoxycarbonyl group, an ethoxycarbonyl group, a propoxycarbonyl group and an isopropoxycarbonyl group, and an amide group including an amino group which may have one or two alkyl groups having 1 to 6 carbon atoms (e.g., an amino group, a methylamino group, a dimethylamino group) and an alicyclic amino group (e.g., a piperidino group, a morpholino group); the term "leaving group" means a leaving group which is used generally in N-alkylation such as a p-toluenesulfonyloxy group, a methanesulfonyloxy group, a chlorine atom, a bromine atom and an iodine atom.

The phenylaminoalkylcarboxylic acid derivatives represented by the above general formula (I) of the present invention can be converted to their pharmaceutically acceptable salts in the usual way. Examples of such salts include acid addition salts formed with mineral acids such as hydrochloric acid, hydrobromic acid, hydroiodic acid, sulfuric acid, nitric acid and phosphoric acid; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid; and inorganic base salts such as a sodium salt, a potassium salt and a calcium salt.

The compounds of the present invention obtained by the above production process can be isolated and purified by conventional separation means such as fractional recrystallization, purification using column chromatography and solvent extraction.

The compounds of the present invention include their solvates with pharmaceutically acceptable solvents such as water and ethanol.

The compounds represented by the above general formula (I) of the present invention and pharmaceutically acceptable salts thereof have excellent $\beta_3$-adrenoceptor stimulating effects and are extremely useful as medicaments such as agents for the prevention or treatment of obesity, hyperglycemia, the diseases caused by intestinal hypermotility, pollakiuria, urinary incontinence, depression, or the diseases caused by biliary calculi or hypermotility of biliary tract.

In the compounds represented by the above general formula (I) of the present invention, compounds wherein the substituent $R^1$ represents a hydroxy group or a lower alkoxy group are preferred and compounds wherein the substituents $R^4$ and $R^5$ independently represent a hydrogen atom or a halogen atom are preferred.

In the compounds represented by the above general formula (I) of the present invention, for example, compounds represented by the general formula:

(Ia)

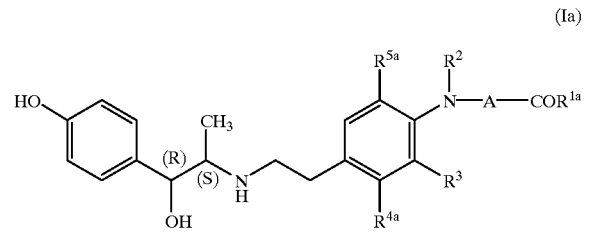

(wherein $R^{1a}$ represents a hydroxy group or a lower alkoxy group; $R^{4a}$ and $R^{5a}$ are the same or different and each represents a hydrogen atom or a halogen atom; and $R^2$, $R^3$, the carbon atom marked with (R) and the carbon atom marked with (S) have the same meanings as defined above) are preferred because these compounds have potent $\beta_3$-adrenoceptor stimulating effects compared with $\beta_1$ and/or $\beta_2$-adrenoceptor stimulating effects thereof and have attenuated side effects caused by $\beta_1$ and/or $\beta_2$-adrenoceptor stimulating effects.

Specially, compounds represented by the general formula:

(Ib)

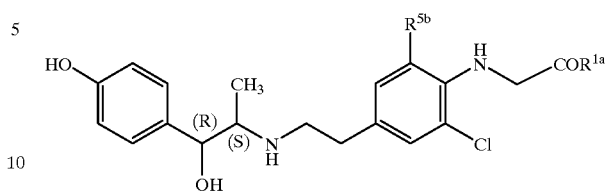

(wherein $R^{5b}$ represents a hydrogen atom or a chlorine atom; and $R^{1a}$, the carbon atom marked with (R) and the carbon atom marked with (S) have the same meanings as defined above) are preferred.

When the phenylaminoalkylcarboxylic acid derivatives represented by the above general formula (I) and pharmaceutically acceptable salts thereof of the present invention are employed in the practical treatment, they are administered orally or parenterally as powders, granules, fine granules, tablets, capsules, injections, solutions, ointments, suppositories and the like. These pharmaceutical compositions can be formulated in accordance with conventional methods using conventional pharmaceutical carriers, excipients and the like.

The dosage is appropriately decided depending on the age, sex, body weight, and degree of symptoms of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

BEST MODE FOR CARRYING OUT THE INVENTION

The present invention is further illustrated in more detail by way of the following Reference Examples, Examples and Test Examples. The present invention is not limited thereto.

Reference Example 1

4-(2-Bromoethyl)aniline hydrobromide

To 4-aminophenethyl alcohol (25 g) was added 48% hydrobromic acid (250 ml), and the mixture was heated under reflux for 4 hours with stirring. After cooling, collection of the resulting precipitates by filtration gave 4-(2-bromoethyl)aniline hydrobromide (30.3 g).

$^1$H-NMR (DMSO-$d_6$) δ ppm: 3.15 (2H, t, J=7.0 Hz), 3.74 (2H, t, J=7.0 Hz), 7.25 (2H, d, J=8.0 Hz), 7.38 (2H, d, J=8.0 Hz), 9.70 (2H, br)

Reference Example 2

Ethyl N-[4-(2-bromoethyl)phenyl]aminoacetate

To a solution of 4-(2-bromoethyl)aniline hydrobromide (9.15 g) in N,N-dimethylformamide (65 ml) were added potassium carbonate (4.95 g) and ethyl bromoacetate (3.97 ml), and the mixture was stirred for 36 hours at room temperature. The reaction mixture was poured into ice-water, and collection of the resulting precipitates by filtration gave ethyl N-[4-(2-bromoethyl)phenyl]aminoacetate (8.39 g)

$^1$H-NMR (CDCl$_3$) δ ppm: 1.29 (3H, t, J=7.1 Hz), 3.04 (2H, t, J=7.8 Hz), 3.49 (2H, t, J=7.8 Hz), 3.88 (2H, s), 4.15–4.35 (2H, m), 6.56 (2H, d, J=8.5 Hz), 7.02 (2H, d, J=8.5 Hz)

Reference Example 3

2-[[4-(2-Bromoethyl)phenyl]amino]-N,N-dimethylacetamide

2-[[4-(2-Bromoethyl)phenyl]amino]-N,N-dimethylacetamide was prepared according to a similar manner to that described in Reference Example 2 using 2-bromo-N,N-dimethylacetamide.

$^1$H-NMR (CDCl$_3$) δ ppm: 2.95–3.10 (8H, m), 3.50 (2H, t, J=7.8 Hz), 3.84 (2H, s), 4.87 (1H, br s), 6.58 (2H, d, J=8.5 Hz), 7.03 (2H, d, J=8.5 Hz)

Reference Example 4

Ethyl N-[4-(2-hydroxyethyl)phenyl]aminoacetate

To a solution of 4-aminophenethyl alcohol (25 g) in N,N-dimethylformamide (500 ml) were added potassium carbonate (30 g) and ethyl bromoacetate (24 ml), and the mixture was stirred for 16 hours at room temperature. Diethylamine (38 ml) was added to the reaction mixture, and the resulting mixture was stirred for 1 hour. The insoluble material was filtered off and the filtrate was concentrated in vacuo. To the residue was added diethyl ether, and the resulting insoluble material was filtered off. The filtrate was washed with 10% aqueous citric acid solution, a saturated aqueous sodium bicarbonate solution and brine subsequently, and dried over anhydrous magnesium sulfate. Removal of the solvent in vacuo gave ethyl N-[4-(2-hydroxyethyl)phenyl]aminoacetate (35.5 g).

$^1$H-NMR (CDCl$_3$) δ ppm: 1.20–1.40 (4H, m), 2.76 (2H, t, J=6.5 Hz), 3.75–3.85 (2H, m), 3.88 (2H, d, J=4.4 Hz), 4.15–4.30 (3H, m), 6.58 (2H, d, J=8.3 Hz), 7.05 (2H, d, J=8.3 Hz)

Reference Example 5

Ethyl 4-[[4-(2-hydroxyethyl)phenyl]amino]butyrate

Ethyl 4-[[4-(2-hydroxyethyl)phenyl]amino]butyrate was prepared according to a similar manner to that described in Reference Example 4 using ethyl 4-bromobutyrate.

$^1$H-NMR (CDCl$_3$) δ ppm: 1.25 (3H, t, J=7.1 Hz), 1.46 (1H, br), 1.85–2.00 (2H, m), 2.42 (2H, t, J=7.2 Hz), 2.75 (2H, t, J=6.5 Hz), 3.16 (2H, t, J=6.9 Hz), 3.65 (1H, br), 3.70–3.85 (2H, m), 4.14 (2H, q, J=7.1 Hz), 6.57 (2H, d, J=8.4 Hz), 7.03 (2H, d, J=8.4 Hz)

Reference Example 6

Ethyl N-[2,6-dibromo-4-(2-bromoethyl)phenyl]aminoacetate

To a stirred solution of ethyl N-[4-(2-bromoethyl)phenyl]aminoacetate (516 mg) in acetonitrile (3.6 ml) were added concentrated hydrochloric acid (150 μl) and N-bromosuccinimide (641 mg) under ice-cooling, and the mixture was stirred for 1 hour. Ethanol (3.6 ml) was added to the reaction mixture, and the mixture was stirred for 30 minutes under ice-cooling. 0.4M Aqueous sodium thiosulfate solution (9.0 ml) was added to the reaction mixture, and the mixture was stirred for 1 hour under ice-cooling. The reaction mixture was diluted with water and extracted with ethyl acetate. The extract was washed with brine and dried over anhydrous magnesium sulfate, and the solvent was removed in vacuo. Purification of the residue by medium pressure liquid column chromatography on silica gel (eluent: hexane/ethyl acetate=6/1) gave ethyl N-[2,6-dibromo-4-(2-bromoethyl)phenyl]aminoacetate (842 mg).

$^1$H-NMR (CDCl$_3$) δ ppm: 1.29 (3H, t, J=7.1 Hz), 3.03 (2H, t, J=7.4 Hz), 3.50 (2H, t, J=7.4 Hz), 4.12 (2H, d, J=5.7 Hz), 4.24 (2H, q, J=7.1 Hz), 4.78 (1H, t, J=5.7 Hz), 7.32 (2H, s)

Reference Example 7

Ethyl N-[2-bromo-4-(2-bromoethyl)phenyl]aminoacetate

Ethyl N-[2-bromo-4-(2-bromoethyl)phenyl]aminoacetate was prepared according to a similar manner to that described in Reference Example 6 using 1 molar equivalent of both N-bromosuccinimide and 0.4M aqueous sodium thiosulfate solution to ethyl N-[4-(2-bromo-ethyl)phenyl]aminoacetate.

$^1$H-NMR (CDCl$_3$) δ ppm: 1.30 (3H, t, J=7.1 Hz), 3.03 (2H, t, J=7.6 Hz), 3.49 (2H, t, J=7.6 Hz), 3.93 (2H, s), 4.26 (2H, q, J=7.1 Hz), 4.90 (1H, br s), 6.46 (1H, d, J=8.2 Hz), 7.03 (1H, dd, J=8.2, 2.0 Hz), 7.31 (1H, d, J=2.0 Hz)

Reference Example 8

Ethyl N-[4-(2-bromoethyl)-2-iodophenyl]aminoacetate

To a stirred solution of ethyl N-[4-(2-bromoethyl)-phenyl]aminoacetate (580 mg) in acetonitrile (4.05 ml) were added concentrated hydrochloric acid (169 μl) and N-iodosuccinimide (912 mg) under ice-cooling, and the mixture was stirred for 1 hour. Ethanol (4.0 ml) was added to the reaction mixture, and the mixture was stirred for 45 minutes under ice-cooling. A solution of sodium thiosulfate (640 mg) in water (20 ml) was added to the reaction mixture, and the mixture was stirred for 1 hour under ice-cooling. The reaction mixture was diluted with water and extracted with ethyl acetate. The extract was washed with brine and dried over anhydrous magnesium sulfate, and the solvent was removed in vacuo. Purification of the residue by medium pressure liquid column chromatography on silica gel (eluent: hexane/ethyl acetate=9/1) gave ethyl N-[4-(2-bromoethyl)-2-iodophenyl]aminoacetate (449 mg).

$^1$H-NMR (CDCl$_3$) δ ppm: 1.31 (3H, t, J=7.1 Hz), 3.01 (2H, t, J=7.6 Hz), 3.48 (2H, t, J=7.6 Hz), 3.92 (2H, d, J=5.3 Hz), 4.26 (2H, q, J=7.1 Hz), 4.75–4.85 (1H, m), 6.39 (1H, d, J=8.2 Hz), 7.06 (1H, dd, J=8.2, 1.9 Hz), 7.54 (1H, d, J=1.9 Hz)

Reference Example 9

2-[[4-(2-Bromoethyl)-2,6-dichlorophenyl]amino]-N,N-dimethylacetamide

To a stirred solution of 2-[[4-(2-bromoethyl)phenyl]-amino]-N,N-dimethylacetamide (1.13 g) in acetonitrile (11.3 ml) were added concentrated hydrochloric acid (331 μl) and N-chloro-succinimide (1.06 g) under ice-cooling, and the mixture was stirred for 1 hour. A solution of sodium thiosulfate (1.26 g) in water (20 ml) was added to the reaction mixture, and the resulting mixture was stirred for 30 minutes under ice-cooling. The reaction mixture was diluted with water and extracted with ethyl acetate. The extract was washed with brine and dried over anhydrous magnesium sulfate, and the solvent was removed in vacuo. Purification of the residue by medium pressure liquid column chromatography on silica gel (eluent: hexane/ethyl acetate=2/1) gave 2-[[4-(2-bromoethyl)-2,6-dichlorophenyl]amino]-N,N-dimethylacetamide (795 mg).

$^1$H-NMR (CDCl$_3$) δ ppm: 2.95–3.05 (8H, m), 3.49 (2H, t, J=7.4 Hz), 4.14 (2H, d, J=4.4 Hz), 5.65–5.75 (1H, m), 7.08 (2H, s)

Reference Example 10

Ethyl N-[2,6-dichloro-4-(2-hydroxyethyl)phenyl]aminoacetate

To a stirred solution of ethyl N-[4-(2-hydroxyethyl)-phenyl]aminoacetate (1.0 g) in dichloromethane (20 ml) were added concentrated hydrochloric acid (373 µl) and ethanol (3.0 ml) at room temperature, and a solution of tert-butyl hypochlorite (1.04 ml) in dichloromethane (6 ml) was added dropwise over 10 minutes period under ice-cooling with stirring. The mixture was stirred for 10 minutes, and the reaction mixture was concentrated in vacuo. A saturated aqueous sodium bicarbonate solution was added to the residue, and the resulting mixture was extracted with ethyl acetate. The extract was washed with brine and dried over anhydrous magnesium sulfate, and the solvent was removed in vacuo. Purification of the residue by medium pressure liquid column chromatography on silica gel (eluent: hexane/ethyl acetate=3/1) gave ethyl N-[2,6-dichloro-4-(2-hydroxyethyl)phenyl]aminoacetate (695 mg).

$^1$H-NMR (CDCl$_3$) δ ppm: 1.28 (3H, t, J=7.1 Hz), 2.74 (2H, t, J=6.4 Hz), 3.82 (2H, t, J=6.4 Hz), 4.14 (2H, s), 4.23 (2H, q, J=7.1 Hz), 7.12 (2H, s)

Reference Example 11

Ethyl 4-[[2,6-dichloro-4-(2-hydroxyethyl)phenyl]amino]butyrate

Ethyl 4-[[2,6-dichloro-4-(2-hydroxyethyl)phenyl]amino]-butyrate was prepared according to a similar manner to that described in Reference Example 10 using ethyl 4-[[4-(2-hydroxyethyl)-phenyl]amino]butyrate.

$^1$H-NMR (CDCl$_3$) δ ppm: 1.26 (3H, t, J=7.1 Hz), 1.44 (1H, br), 1.85–1.95 (2H, m), 2.43 (2H, t, J=7.4 Hz), 2.74 (2H, t, J=6.4 Hz), 3.33 (2H, t, J=7.1 Hz), 3.75–3.95 (3H, m), 4.14 (2H, q, J=7.1 Hz), 7.12 (2H, s)

Reference Example 12

Ethyl N-[4-(2-hydroxyethyl)phenyl]-N-methylaminoacetate

To a solution of ethyl N-[4-(2-hydroxyethyl)phenyl]-aminoacetate (1.15 g) in N,N-dimethylformamide (10 ml) were added potassium carbonate (1.17 g) and methyl iodide (420 µl), and the mixture was stirred for 9 hours at room temperature. The reaction mixture was poured into water and extracted with ethyl acetate. The extract was washed with brine and dried over anhydrous magnesium sulfate, and the solvent was removed in vacuo. Purification of the residue by flash column chromatography on silica gel (eluent: dichloromethane/diethyl ether=10/1) gave ethyl N-[4-(2-hydroxyethyl)phenyl]-N-methylaminoacetate (820 mg).

$^1$H-NMR (CDCl$_3$) δ ppm: 1.25 (3H, t, J=7.1 Hz), 1.51 (1H, br), 2.77 (2H, t, J=6.5 Hz), 3.05 (3H, s), 3.80 (2H, t, J=6.5 Hz), 4.04 (2H, s), 4.18 (2H, q, J=7.1 Hz), 6.65 (2H, d, J=8.8 Hz), 7.09 (2H, d, J=8.8 Hz)

Reference Example 13

Ethyl N-[2,6-dichloro-4-(2-hydroxyethyl)phenyl]-N-methylaminoacetate

Ethyl N-[2,6-dichloro-4-(2-hydroxyethyl)phenyl]-N-methyl-aminoacetate was prepared according to a similar manner to that described in Reference Example 12 using the corresponding ethyl aminoacetate derivative.

$^1$H-NMR (CDCl$_3$) δ ppm: 1.26 (3H, t, J=7.1 Hz), 1.41 (1H, br), 2.70–2.80 (2H, m), 2.94 (3H, s), 3.80–3.90 (4H, m), 4.17 (2H, q, J=7.1 Hz), 7.10–7.20 (2H, m)

Reference Example 14

Ethyl N-[2-chloro-4-(2-hydroxyethyl)phenyl]aminoacetate

To a stirred solution of 4-amino-3-chlorophenethyl alcohol (950 mg) and triethylamine (2.3 ml) in tetrahydrofuran (5.5 ml) was added a solution of trifluoroacetic anhydride (1.6 ml) in tetrahydrofuran (2.0 ml) under ice-cooling, and the mixture was stirred for 10 minutes. To the reaction mixture was added methanol (2.0 ml), and the resulting mixture was stirred for 5 minutes. 1N Hydrochloric acid (10 ml) was added to the stirred mixture, and the resulting mixture was extracted with ethyl acetate. The extract was washed with a saturated aqueous sodium bicarbonate solution and brine subsequently, and dried over anhydrous magnesium sulfate. Removal of the solvent in vacuo gave 2'-chloro-4'-(2-hydroxyethyl)-2,2,2-trifluoroacetanilide (1.4 g).

$^1$H-NMR (CDCl$_3$) δ ppm: 2.86 (2H, t, J=6.4 Hz), 3.87 (2H, t, J=6.4 Hz), 7.22 (1H, dd, J=8.4, 2.0 Hz), 7.35 (1H, d, J=2.0 Hz), 8.24 (1H, d, J=8.4 Hz), 8.36 (1H, br)

To a solution of 2'-chloro-4'-(2-hydroxyethyl)-2,2,2-trifluoroacetanilide (1.4 g) and 3,4-dihydro-2H-pyran (1.4 ml) in dichloromethane (15 ml) was added pyridinium p-toluenesulfonate (14 mg), and the mixture was heated under reflux for 1 hour with stirring. After concentration of the reaction mixture in vacuo, the residue was dissolved in ethyl acetate. The solution was washed with a saturated aqueous sodium bicarbonate solution and brine, and dried over anhydrous magnesium sulfate, and the solvent was removed in vacuo. Purification of the residue by medium pressure liquid column chromatography on silica gel (eluent: hexane/diethyl ether=3/1) gave 2'-chloro-4'-[2-((RS)-tetrahydropyran-2-yloxy)ethyl]-2,2,2-trifluoroacetanilide (1.4 g).

$^1$H-NMR (CDCl$_3$) δ ppm: 1.40–1.90 (6H, m), 2.88 (2H, t, J=6.7 Hz), 3.40–3.50 (1H, m), 3.60 (1H, dt, J=9.8, 6.7 Hz), 3.65–3.80 (1H, m), 3.94 (1H, dt, J=9.8, 6.7 Hz), 4.55–4.60 (1H, m), 7.23 (1H, dd, J=8.4, 1.9 Hz), 7.36 (1H, d, J=1.9 Hz), 8.22 (1H, d, J=8.4 Hz), 8.36 (1H, br)

To a stirred solution of 2'-chloro-4'-[2-((RS)-tetrahydropyran-2-yloxy)ethyl]-2,2,2-trifluoroacetanilide (352 mg) in N,N-dimethylformamide (3 ml) was added sodium hydride (48 mg) under ice-cooling, and the mixture was stirred for 30 minutes at room temperature. Ethyl bromoacetate (133 µl) was added to the reaction mixture, and the mixture was stirred for 16 hours. Ethyl acetate was added to the reaction mixture, and the resulting mixture was washed with brine and dried over anhydrous magnesium sulfate. After the solvent was removed in vacuo, purification of the residue by medium pressure liquid column chromatography on silica gel (eluent: hexane/diethyl ether=2/1) gave ethyl N-[2-chloro-4-[2-((RS)-tetrahydropyran-2-yloxy)ethyl]phenyl]-N-trifluoroacetylamino-acetate (250 mg).

$^1$H-NMR (CDCl$_3$) δ ppm: 1.28 (3H, t, J=7.1 Hz), 1.40–1.85 (6H, m), 2.91 (2H, t, J=6.6 Hz), 3.40–3.50 (1H, m), 3.55–3.70 (2H, m), 3.72 (1H, d, J=17.2 Hz), 3.90–4.00 (1H, m), 4.15–4.30 (2H, m), 4.55–4.65 (1H, m), 4.98 (1H, d, J=17.2 Hz), 7.15–7.25 (1H, m), 7.35–7.45 (1H, m), 7.56 (1H, d, J=8.1 Hz)

A solution of ethyl N-[2-chloro-4-[2-((RS)-tetrahydropyran-2-yloxy)ethyl]phenyl]-N-trifluoroacetylaminoacetate (830 mg) and p-toluenesulfonic acid monohydrate (80 mg) in ethanol (9.0 ml) was stirred for 2 hours at 40° C. To the reaction mixture was added potassium carbonate (314 mg), and the resulting mixture was heated under reflux for 5 hours with stirring. The insoluble material was filtered off, the filtrate was concentrated in vacuo, and the residue was dissolved in ethyl acetate. The solution was washed with a saturated aqueous sodium bicarbonate solution and brine, and dried over anhydrous magnesium sulfate, and the solvent was removed in vacuo. Purification of the residue by medium pressure liquid column chromatography on silica gel (eluent: hexane/ethyl acetate=2/1) gave ethyl N-[2-chloro-4-(2-hydroxyethyl)phenyl]aminoacetate (315 mg).

$^1$H-NMR (CDCl$_3$) δ ppm: 1.30 (3H, t, J=7.1 Hz), 1.37 (1H, br s), 2.74 (2H, t, J=6.5 Hz), 3.75–3.85 (2H, m), 3.93 (2H, d, J=5.5 Hz), 4.26 (2H, q, J=7.1 Hz), 4.80–4.90 (1H, m), 6.49 (1H, d, J=8.2 Hz), 7.00 (1H, dd, J=8.2, 2.0 Hz), 7.17 (1H, d, J=2.0 Hz)

Reference Example 15

Ethyl N-[2-chloro-4-(2-hydroxyethyl)phenyl]-N-methylaminoacetate

Ethyl N-[2-chloro-4-(2-hydroxyethyl)phenyl]-N-methylaminoacetate was prepared according to a similar manner to that described in Reference Example 12 using the corresponding ethyl aminoacetate derivative.

$^1$H-NMR (CDCl$_3$) δ ppm: 1.24 (3H, t, J=7.1 Hz), 1.35–1.50 (1H, m), 2.78 (2H, t, J=6.5 Hz), 2.97 (3H, s), 3.75–3.90 (2H, m), 3.96 (2H, s), 4.15 (2H, q, J=7.1 Hz), 7.07 (1H, dd, J=8.2, 1.9 Hz), 7.14 (1H, d, J=8.2 Hz), 7.21 (1H, d, J=1.9 Hz)

Reference Example 16

Ethyl N-[4-(2-bromoethyl)-2,6-dichlorophenyl] aminoacetate

To a stirred solution of ethyl N-[2,6-dichloro-4-(2-hydroxyethyl)phenyl]aminoacetate (650 mg) and triphenylphosphine (700 mg) in dichloromethane (10ml) was added carbon tetrabromide (886 mg) under ice-cooling, and the mixture was stirred for 1 hour. Rough purification of the reaction mixture by flash column chromatography on silica gel (eluent: hexane/ethyl acetate=3/1) and further purification of the fraction by medium pressure liquid column chromatography on silica gel (eluent: hexane/dichloromethane=1/1) gave ethyl N-[4-(2-bromoethyl)-2,6-dichlorophenyl]-aminoacetate (708 mg).

$^1$H-NMR (CDCl$_3$) δ ppm: 1.28 (3H, t, J=7.2 Hz), 3.03 (2H, t, J=7.4 Hz), 3.50 (2H, t, J=7.4 Hz), 4.16 (2H, d, J=5.7 Hz), 4.23 (2H, q, J=7.2 Hz), 4.80–4.90 (1H, m), 7.10 (2H, s)

Reference Example 17

The following compounds were prepared according to a similar manner to that described in Reference Example 16 using the corresponding hydroxyethyl derivative.

Ethyl N-[4-(2-bromoethyl)phenyl]aminoacetate $^1$H-NMR (CDCl$_3$) δ ppm: 1.29 (3H, t, J=7.1 Hz), 3.04 (2H, t, J=7.8 Hz), 3.50 (2H, t, J=7.8 Hz), 3.88 (2H, s), 4.24 (2H, q, J=7.1 Hz), 6.56 (2H, d, J=8.5 Hz), 7.02 (2H, d, J=8.5 Hz)

Ethyl N-[4-(2-bromoethyl)phenyl]-N-methylaminoacetate $^1$H-NMR (CDCl$_3$) δ ppm: 1.24 (3H, t, J=7.1 Hz), 3.00–3.10(5H, m), 3.50 (2H, t, J=7.9 Hz), 4.04 (2H, s), 4.17 (2H, q, J=7.1 Hz), 6.64 (2H, d, J=8.8 Hz), 7.07 (2H, d, J=8.8 Hz)

Ethyl N-[4-(2-bromoethyl)-2-chlorophenyl] aminoacetate $^1$H-NMR (CDCl$_3$) δ ppm: 1.30 (3H, t, J=7.1 Hz), 3.03 (2H, t, J=7.6 Hz), 3.49 (2H, t, J=7.6 Hz), 3.93 (2H, d, J=5.5 Hz), 4.26 (2H, q, J=7.1 Hz), 4.85–4.95 (1H, m), 6.49 (1H, d, J=8.3 Hz), 6.98 (1H, dd, J=8.3, 2.0 Hz), 7.14 (1H, d, J=2.0 Hz)

Ethyl N-[4-(2-bromoethyl)-2-chlorophenyl]-N-methylaminoacetate $^1$H-NMR (CDCl$_3$) δ ppm: 1.24 (3H, t, J=7.1 Hz), 2.97 (3H, s), 3.07 (2H, t, J=7.6 Hz), 3.52 (2H, t, J=7.6 Hz), 3.97 (2H, s), 4.15 (2H, q, J=7.1 Hz), 7.04 (1H, dd, J=8.2, 2.0 Hz), 7.13 (1H, d, J=8.2 Hz), 7.18 (1H, d, J=2.0 Hz)

Ethyl N-[4-(2-bromoethyl)-2,6-dichlorophenyl]-N-methylaminoacetate $^1$H-NMR (CDCl$_3$) δ ppm: 1.26 (3H, t, J=7.1 Hz), 2.95 (3H, s), 3.06 (2H, t, J=7.3 Hz), 3.52 (2H, t, J=7.3 Hz), 3.88 (2H, s), 4.17 (2H, q, J=7.1 Hz), 7.14 (2H, s)

Ethyl 4-[[4-(2-bromoethyl)-2,6-dichlorophenyl] amino]butyrate $^1$H-NMR (CDCl$_3$) δ ppm: 1.26 (3H, t, J=7.1 Hz), 1.85–1.95 (2H, m), 2.43 (2H, t, J=7.4 Hz), 3.02 (2H, t, J=7.4 Hz), 3.30–3.40 (2H,m), 3.50 (2H, t, J=7.4 Hz), 3.93 (1H, br), 4.14 (2H, q, J=7.1 Hz), 7.09 (2H, s)

Reference Example 18

Ethyl N-[4-(2-bromoethyl)-3-chlorophenyl] aminoacetate

To a stirred solution of 2-chloro-4-nitrophenethyl alcohol (1.17 g) in dichloromethane (15 ml) were added carbon tetrabromide (2.12 g) and triphenylphosphine (1.67 g) at room temperature, and the mixture was stirred for 15 minutes. The solvent was removed in vacuo, and purification of the residue by flash column chromatography on silica gel (eluent: hexane/ethyl acetate=9/1) gave 1-(2-bromo-ethyl)-2-chloro-4-nitrobenzene (1.30 g).

$^1$H-NMR (CDCl$_3$) δ ppm: 3.40 (2H, t, J=7.0 Hz), 3.64 (2H, t, J=7.0 Hz), 7.48 (1H, d, J=8.4 Hz), 8.11 (1H, dd, J=8.4, 2.2 Hz), 8.27 (1H, d, J=2.2 Hz)

To a solution of 1-(2-bromoethyl)-2-chloro-4-nitrobenzene (1.24 g) in methanol (20 ml) were added 2N hydrochloric acid (7.0 ml) and iron powder (785 mg), and the mixture was heated under reflux for 50 minutes with stirring. After the insoluble material was filtered off, the filtrate was alkalized with 2N aqueous sodium hydroxide solution and extracted with dichloromethane. The extract was washed with brine and dried over anhydrous magnesium sulfate, and the solvent was removed in vacuo. The residue was dissolved in N,N-dimethylformamide (10 ml), and potassium carbonate (647 mg) andethyl bromoacetate (520 μl) were added to the solution. After the mixture was stirred for 14 hours at room temperature, water was added to the reaction mixture, and the resulting mixture was extracted with a mixed solution of diethyl ether and ethyl acetate (3/1). The extract was washed with water and brine subsequently, and dried over anhydrous magnesium sulfate, and the solvent was removed in vacuo. Purification of the residue by flash column chromatography on silica gel (eluent: hexane/ethyl acetate=4/1) gave ethyl N-[4-(2-bromoethyl)-3-chlorophenyl]aminoacetate (426 mg).

$^1$H-NMR (CDCl$_3$) δ ppm: 1.30 (3H, t, J=7.1 Hz), 3.00–3.20 (2H, m), 3.45–3.70 (2H, m), 3.86 (2H, d, J=5.3

Hz), 4.25 (2H, q, J=7.1 Hz), 4.34 (1H, br), 6.40–6.50 (1H, m), 6.55–6.65 (1H, m), 7.00–7.10 (1H, m)

Reference Example 19

Ethyl N-[4-(2-bromoethyl)-2,3-dichlorophenyl] aminoacetate Ethyl N-[4-(2-bromoethyl)-2,5-dichlorophenyl]aminoacetate To a stirred solution of ethyl N-[4-(2-bromoethyl)-3-chlorophenyl]aminoacetate (79 mg) in dichloromethane (2 ml) was added tert-butyl hypochlorite (31 μl) under ice-cooling, and the mixture was stirred for 6 hours at room temperature. The solvent was removed in vacuo, and purification of the residue by flash column chromatography on silica gel (eluent: hexane/ethyl acetate=15/1) gave ethyl N-[4-(2-bromoethyl) -2,3-dichlorophenyl]aminoacetate (31 mg) as a high-polar regioisomer and ethyl N-[4-(2-bromoethyl)-2,5-dichlorophenyl]aminoacetate (34 mg) as a low-polar regioisomer.

Ethyl N-[4-(2-bromoethyl)-2,3-dichlorophenyl] aminoacetate $^1$H-NMR (CDCl$_3$) δ ppm: 1.30 (3H, t, J=7.1 Hz), 3.05–3.25 (2H, m), 3.50–3.70 (2H, m), 3.94 (2H, d, J=5.4 Hz), 4.26 (2H, q, J=7.1 Hz), 5.04 (1H, br), 6.41 (1H, d, J=8.4 Hz), 7.05 (1H, d, J=8.4 Hz)

Ethyl N-[4-(2-bromoethyl)-2,5-dichlorophenyl] aminoacetate $^1$H-NMR (CDCl$_3$) δ ppm: 1.31 (3H, t, J=7.1 Hz), 3.00–3.20 (2H, m), 3.45–3.70 (2H, m), 3.90 (2H, d, J=5.3 Hz), 4.27 (2H, q, J=7.1 Hz), 4.95 (1H, br), 6.53 (1H, s), 7.17 (1H, s)

Reference Example 20

Ethyl N-[4-(2-bromoethyl)-2,3,6-trichlorophenyl] aminoacetate

To a stirred solution of ethyl N-[4-(2-bromoethyl)-3-chlorophenyl]aminoacetate (513 mg) in dichloromethane (4 ml) was added tert-butyl hypochlorite (370 μl) under ice-cooling, and the mixture was stirred for 10 minutes. The solvent was removed in vacuo, and purification of the residue by flash column chromatography on silica gel (eluent: hexane/ethyl acetate=10/1) gave ethyl N-[4-(2-bromoethyl)-2,3,6-trichlorophenyl]aminoacetate (453 mg).

$^1$H-NMR (CDCl$_3$) δ ppm: 1.29 (3H, t, J=7.1 Hz), 3.21 (2H, t, J=7.3 Hz), 3.54 (2H, t, J=7.3 Hz), 4.17 (2H, s), 4.24 (2H, q, J=7.1 Hz), 4.98 (1H, br), 7.17 (1H, s)

Reference Example 21

Ethyl N-]4-(2-bromoethyl)-2,5-dimethylphenyl] aminoacetate

To a stirred solution of 2,5-dimethylaniline (5.30 g) and 4-dimethylaminopyridine (6.41 g) in dichloromethane (90 ml) was added acetic anhydride (4.13 ml) under ice-cooling, and the mixture was stirred for 4 hours. The reaction mixture was washed with 1N hydrochloric acid and a saturated aqueous sodium bicarbonate solution subsequently, and dried over anhydrous magnesium sulfate. Removal of the solvent in vacuo gave 2',5'-dimethylacetanilide (6.09 g).

$^1$H-NMR (CDCl$_3$) δ ppm: 2.20 (3H, s), 2.21 (3H, s), 2.31 (3H, s), 6.80–7.00 (2H, m), 7.06 (1H, d, J=7.7 Hz), 7.59 (1H, s)

To a stirred suspension of aluminum chloride (13.4 g) in carbon disulfide (68 ml) was added bromoacetyl bromide (8.8 ml) under ice-cooling, and the mixture was stirred for 30 minutes. 2',5'-Dimethylacetanilide (5.57 g) was added to the stirred mixture, and the mixture was heated under reflux for 12 hours. After cooling, the reaction mixture was poured into ice-water, and the resulting precipitate were collected by filtration and washed with water. The cake was dissolved in ethyl acetate, and the solution was dried over anhydrous magnesium sulfate. After removal of the solvent, the residue was washed with diethyl ether to give 4'-(2-bromo-acetyl)-2',5'-dimethylacetanilide (5.65 g).

$^1$H-NMR (CDCl$_3$) δ ppm: 2.24 (3H, s), 2.29 (3H, s), 2.52 (3H, s), 4.38 (2H, s), 7.03 (1H, br), 7.53 (1H, s), 7.98 (1H, br)

To a stirred solution of 4'-(2-bromoacetyl)-2',5'-dimethylacetanilide (4.57 g) in ethanol (80 ml) was added sodium borohydride (608 mg) under ice-cooling, and the mixture was stirred for 1 hour. Acetic acid (3.7 ml) and water (200 ml) were added to the reaction mixture, and the resulting mixture was extracted with ethyl acetate. The extract was washed with water and brine, and dried over anhydrous magnesium sulfate, and the solvent was removed in vacuo. The residue was dissolved in tetrahydrofuran (80 ml), and 5N aqueous sodium hydroxide solution (6.4 ml) was added to the solution under ice-cooling with stirring. The mixture was stirred for 30 minutes at room temperature, water was added to the reaction mixture, and the resulting mixture was extracted with ethyl acetate. The extract was washed with water and dried over anhydrous magnesium sulfate, and the solvent was removed in vacuo. To the residue was added diethyl ether, and collection of the insoluble material by filtration gave 2',5'-dimethyl-4'-oxiranylacetanilide (1.72 g).

$^1$H-NMR (CDCl$_3$) δ ppm: 2.20 (6H, s), 2.37 (3H, s), 2.60–2.70 (1H, m), 3.10–3.20 (1H, m), 3.90–4.00 (1H, m), 6.90 (1H, br), 7.00 (1H, s), 7.61 (1H, s)

2',5'-Dimethyl-4'-oxiranylacetanilide (1.61 g) and 10% palladium carbon (13 mg) was suspended in ethanol (90 ml), and the mixture was stirred for 2.5 hours at room temperature under a hydrogen atmosphere. The insoluble material was filtered off, and the filtrate was concentrated in vacuo. 6N Hydrochloric acid (15 ml) was added to the residue, and the mixture was heated under reflux for 2 hours. After cooling, water was added to the reaction mixture, and the mixture was washed with ethyl acetate. 5N Aqueous sodium hydroxide solution (20 ml) was added to the mixture and the resulting mixture was extracted with ethyl acetate. The extract was washed with brine and dried over anhydrous magnesium sulfate, and the solvent was removed in vacuo. The residue was dissolved in 48% hydrobromic acid (10 ml), and the solution was stirred for 3.5 hours at 120° C. The reaction mixture was poured into a saturated aqueous sodium bicarbonate solution under ice-cooling with stirring, and the resulting mixture was extracted with ethyl acetate. The extract was washed with brine and dried over anhydrous magnesium sulfate, and the solvent was removed in vacuo. After the residue was dissolved in N,N-dimethylformamide (35 ml), potassium carbonate (1.61 g) and ethyl bromoacetate (785 μl) were added to the solution at room temperature with stirring. After the mixture was stirred for 15.5 hours, water was added to the reaction mixture, and the resulting mixture was extracted with ethyl acetate. The extract was washed with water and dried over anhydrous magnesium sulfate, and the solvent was removed in vacuo. Purification of the residue by flash column chromatography on silica gel (eluent: hexane/ethyl acetate=10/1) gave ethyl N-[4-(2-bromoethyl)-2,5-dimethylphenyl]aminoacetate (592 mg).

¹H-NMR (CDCl₃) δ ppm: 1.31 (3H, t, J=7.1 Hz), 2.16 (3H, s), 2.26 (3H, s), 3.00–3.10 (2H, m), 3.40–3.50 (2H, m), 3.91 (2H, d, J=5.2 Hz), 4.05–4.15 (1H, m), 4.26 (2H, q, J=7.1 Hz), 6.28 (1H, s), 6.85 (1H, s)

EXAMPLE 1

Ethyl N-[2,6-dichloro-4-[2-[[(1S, 2R)-2-hydroxy-2-(4-hydroxy-phenyl)-1-methylethyl]amino]ethyl] phenyl]aminoacetate (Compound 1)

To a solution of (1R,2S)-2-amino-1-(4-hydroxyphenyl)-propan-1-ol (495 mg) and ethyl N-[4-(2-bromoethyl)-2,6-dichloro-phenyl]aminoacetate (700 mg) in N,N-dimethylformamide (6 ml) was added N,N-diisopropylethylamine (343 μl), and the mixture was stirred for 7 hours at 70° C. The reaction mixture was concentrated in vacuo, and purification of the residue by medium pressure liquid column chromatography on aminopropyl silica gel (eluent: dichloro-methane/ethanol=20/1) gave ethyl N-[2,6-dichloro-4-[2-[[(1S, 2R)-2-hydroxy-2-(4-hydroxyphenyl)-1-methylethyl]amino]-ethyl]phenyl]aminoacetate (510 mg).

¹H-NMR (CDCl₃) δ ppm: 0.95 (3H, d, J=6.4 Hz), 1.30 (3H, t, J=7.2 Hz), 2.55–3.05 (5H, m), 4.16 (2H, d, J=6.0 Hz), 4.25 (2H, q, J=7.2 Hz), 4.51 (1H, d, J=5.3 Hz), 4.78 (1H, t, J=6.0 Hz), 6.75 (2H, d, J=8.5 Hz), 7.00 (2H, s), 7.10 (2H, d, J=8.5 Hz)

EXAMPLE 2

Ethyl N-[2,6-dichloro-4-[2-[[(1S, 2R)-2-hydroxy-2-(4-hydroxy-phenyl)-1-methylethyl]amino]ethyl] phenyl]aminoacetate hydrochloride (Compound 2)

To a stirred solution of ethyl N-[2,6-dichloro-4-[2-[[(1S, 2R)-2-hydroxy-2-(4-hydroxyphenyl)-1-methylethyl] amino]-ethyl]phenyl]aminoacetate (87 ml) in ethyl acetate (2.0 ml) was added 2.6 M hydrogen chloride diethyl ether solution (2.0 ml) at room temperature. Collection of the resulting precipitates by filtration gave ethyl N-[2,6-dichloro-4-[2-[[(1S, 2R)-2-hydroxy-2-(4-hydroxyphenyl)-1-methylethyl]amino]ethyl]phenyl]aminoacetate hydrochloride (81 mg).

¹H-NMR (DMSO-d₆) δ ppm: 0.95 (3H, d, J=6.7 Hz), 1.16 (3H, t, J=7.1 Hz), 2.85–3.00 (2H, m), 3.15–3.40 (3H, m), 4.08 (2H, q, J=7.1 Hz), 4.20 (2H, s), 5.05 (1H, br s), 5.35 (1H, br), 5.94 (1H, br s), 6.76 (2H, d, J=8.6 Hz), 7.16 (2H, d, J=8.6 Hz), 7.28 (2H, s), 8.70 (2H, br), 9.39 (1H, br s)

Specific Rotation: $[\alpha]_D^{30}$=−6.3° (c=0.67, Methanol)

EXAMPLE 3

The following compounds were prepared according to a similar manner to that described in Example 1 or Examples 1–2 using the corresponding aminoacetate derivative.

Ethyl N-[4-[2-[[(1S, 2R)-2-hydroxy-2-(4-hydroxyphenyl)-1-methyl-ethyl]amino]ethyl]phenyl] aminoacetate hydrobromide (Compound 3)

¹H-NMR (DMSO-d₆) δ ppm: 0.94 (3H, d, J=6.7 Hz), 1.19 (3H, t, J=7.1 Hz), 2.82 (2H, t, J=8.3 Hz), 3.05–3.40 (3H, m), 3.86 (2H, d, J=6.4 Hz), 4.10 (2H, q, J=7.1 Hz), 4.98 (1H, br s), 5.90–6.00 (2H, m), 6.52 (2H, d, J=8.5 Hz), 6.75 (2H, d, J=8.5 Hz), 6.98 (2H, d, J=8.5 Hz), 7.16 (2H, d, J=8.5 Hz), 8.47 (2H, br), 9.38 (1H, s)

Ethyl 4-[[2,6-dichloro-4-[2-[(1S, 2R)-2-hydroxy-2-(4-hydroxy-phenyl)-1-methylethyl]amino]ethyl] phenyl]amino]butyrate (Compound 4)

¹H-NMR (CDCl₃) δ ppm: 1.09 (3H, d, J=6.4 Hz), 1.23 (3H, t, J=7.1 Hz), 1.80–1.90 (2H, m), 2.43 (2H, t, J=7.3 Hz), 2.50–2.95 (5H, m), 3.25–3.35 (2H, m), 4.11 (2H, q, J=7.1 Hz), 4.35 (1H, d, J=6.4Hz), 6.71 (2H, d, J=8.6 Hz), 7.04 (2H, s), 7.07 (2H, d, J=8.6 Hz)

Ethyl N-[2-chloro-4-[2-[[(1S, 2R)-2-hydroxy-2-(4-hydroxyphenyl)-1-methylethyl]amino]ethyl]phenyl] aminoacetate (Compound 5)

¹H-NMR (CDCl₃) δ ppm: 0.96 (3H, d, J=6.4 Hz), 1.32 (3H, t, J=7.1 Hz), 2.55–3.00 (5H, m), 3.96 (2H, d, J=5.9 Hz), 4.29 (2H, q, J=7.1 Hz), 4.47 (1H, d, J=5.6 Hz), 4.82 (1H, t, J=5.9 Hz), 6.40 (1H, d, J=8.2 Hz), 6.70 (2H, d, J=8.6 Hz), 6.87 (1H, dd, J=8.2, 1.9 Hz), 7.02 (1H, d, J=1.9 Hz), 7.06 (2H, d, J=8.6 Hz)

Ethyl N-[4-[2-[[(1S, 2R)-2-hydroxy-2-(4-hydroxyphenyl)-1-methyl-ethyl]amino]ethyl] phenyl]-N-methylaminoacetate (Compound 6)

¹H-NMR (CDCl₃) δ ppm: 1.10 (3H, d, J=6.3 Hz), 1.23 (3H, t, J=7.1 Hz), 2.45–2.75 (4H, m), 2.80–2.90 (1H, m), 3.02 (3H, s), 4.10 (2H, s), 4.16 (2H, q, J=7.1 Hz), 4.31 (1H, d, J=6.8 Hz), 6.53 (2H, d, J=8.7 Hz), 6.68 (2H, d, J=8.5 Hz), 6.85 (2H, d, J=8.7 Hz), 7.03 (2H, d, J=8.5 Hz)

Ethyl N-[2,6-dichloro-4-[2-[[(1S, 2R)-2-hydroxy-2-(4-hydroxy-phenyl)-1-methylethyl]amino]ethyl] phenyl]-N-methylaminoacetate (Compound 7)

¹H-NMR (CDCl₃) δ ppm: 0.92 (3H, d, J=6.4 Hz), 1.29 (3H, t, J=7.1 Hz), 2.67 (2H, t J=6.7 Hz), 2.75–3.20 (6H, m), 3.87 (2H, s), 4.21 (2H, q, J=7.1 Hz), 4.53 (1H, d, J=4.9 Hz), 6.76 (2H, d, J=8.5 Hz), 7.08 (2H, s), 7.11 (2H, d, J=8.5 Hz)

Ethyl N-[2-chloro-4-[2-[[(1S, 2R)-2-hydroxy-2-(4-hydroxyphenyl)-1-methylethyl]amino]ethyl]phenyl]-N-methylaminoacetate (Compound 8)

¹H-NMR (CD₃OD) δ ppm: 1.10 (3H, d, J=6.3 Hz), 1.23 (3H, t, J=7.1 Hz), 2.50–2.95 (8H, m), 3.90 (2H, s), 4.15 (2H, q, J=7.1 Hz), 4.33 (1H, d, J=6.6 Hz), 6.69 (2H, d, J=8.5 Hz), 6.88 (1H, d, J=8.2 Hz), 7.00–7.10 (4H, m)

Ethyl N-[2,3-dichloro-4-[2-[[(1S, 2R)-2-hydroxy-2-(4-hydroxy-phenyl)-1-methylethyl]amino]ethyl] phenyl]aminoacetate (Compound 9)

¹H-NMR (CD₃OD) δ ppm: 1.10 (3H, d, J=6.3 Hz), 1.27 (3H, t, J=7.1 Hz), 2.60–2.90 (5H, m), 4.01 (2H, s), 4.22 (2H, q, J=7.1 Hz), 4.34 (1H, d, J=6.6 Hz), 6.36 (1H, d, J=8.4 Hz), 6.70 (2H, d, J=8.5 Hz), 6.81 (1H, d, J=8.4 Hz), 7.07 (2H, d, J=8.5 Hz)

Ethyl N-[2,5-dichloro-4-[2-[[(1S, 2R)-2-hydroxy-2-(4-hydroxy-phenyl) -1-methylethyl]amino]ethyl] phenyl]aminoacetate (Compound 10)

¹H-NMR (CD₃OD) δ ppm: 1.09 (3H, d, J=6.44 Hz), 1.28 (3H, t, J=7.1 Hz), 2.60–2.90 (5H, m), 3.99 (2H, s), 4.23 (2H, q, J=7.1 Hz), 4.36 (1H, d, J=6.5 Hz), 6.51 (1H, s), 6.70 (2H, d, J=8.6 Hz), 7.00–7.15 (3H, m)

Ethyl N-[2,3,6-trichloro-4-[2-[[(1S, 2R)-2-hydroxy-2-(4-hydroxy-phenyl)-1-methylethyl]amino]ethyl] phenyl]aminoacetate (Compound 11)

¹H-NMR (CD₃OD) δ ppm: 1.09 (3H, d, J=6.44 Hz), 1.25 (3H, t, J=7.1 Hz), 2.65–2.95 (5H, m), 4.10–4.25 (4H, m), 4.37 (1H, d, J=6.4 Hz), 6.71 (2H, d, J=8.5 Hz), 7.08 (2H, d, J=8.5 Hz), 7.11 (1H, s)

Ethyl N-[4-[2-[[(1S, 2R)-2-hydroxy-2-(4-hydroxyphenyl)-1-methylethyl]amino]ethyl]-2,5-dimethylphenyl]aminoacetate (Compound 12)

¹H-NMR (CDCl₃) δ ppm: 0.96 (3H, d, J=6.44 Hz), 1.34 (3H, t, J=7.1 Hz), 2.10 (3H, s), 2.22 (3H, s), 2.55–2.95 (5H, m), 3.90–4.10 (3H, m), 4.30 (2H, q, J=7.1 Hz), 4.49 (1H, d, J=5.6 Hz), 6.22 (1H, s), 6.60–6.70 (3H, m), 7.06 (2H, d, J=8.6 Hz)

Ethyl N-[2-bromo-4-[2-[[(1S, 2R)-2-hydroxy-2-(4-hydroxyphenyl) methylethyl]amino]ethyl]phenyl] aminoacetate (Compound 13)

$^1$H-NMR (DMSO-d$_6$) δ ppm: 0.79 (3H, d, J=6.4 Hz), 1.15–1.30 (4H, m), 2.20–2.75 (5H, m), 3.97 (2H, d, J=6.0 Hz), 4.13 (2H, q, J=7.1 Hz), 4.35–4.45 (1H, m), 4.82 (1H, d, J=3.9 Hz) 5.31 (1H, t, J=6.0 Hz), 6.44 (4H, d, J=8.3 Hz), 6.67 (2H, d, J=8.5 Hz), 6.95 (6H, dd, J=8.3, 1.8 Hz), 7.06 (2H, d, J=8.5 Hz), 7.26 (1H, d, J=1.8 Hz), 9.13 (1H, br s) Specific Rotation: [α]$_D^{29}$=−7.1° (c=0.65, Methanol)

Ethyl N-[2,6-dibromo-4-[2-[[(1S, 2R-2-hydroxy-2-(4-hydroxyphenyl)-1-methylethyl]amino]ethyl] phenyl]aminoacetate (Compound 13)

$^1$H-NMR (DMSO-d$_6$) δ ppm: 0.79 (3H, d, J=6.4 Hz), 1.17 (3H, t, J=7.1 Hz), 1.20–1.35 (5H, m), 2.30–2.80 (5H, m), 4.05–4.20 (4H, m), 4.35–4.45 (1H, m), 4.83 (1H, d, J=3.9 Hz), 4.90 (1H, t, J=6.4 Hz), 6.67 (24, d, J=8.5 Hz), 7.06 (2H, d, J=8.5 Hz), 7.38 (2H, s), 9.13 (1H, br s) Specific Rotation: [α]$_D^{29}$=−4.3° (c=0.47, Methanol)

Ethyl N-[4-[2-[[(1S, 2R)-2-hydroxy-2-(4-hydroxyphenyl)-1-methylethyl]amino]ethyl]-2-iodophenyl]aminoacetate (Compound 15)

$^1$H-NMR (CDCl$_3$) δ ppm: 0.96 (3H, d, J=6.3 Hz), 1.33 (3H, t, J=7.1 Hz), 2.55–3.00 (6H, m), 3.95 (2H, d, J=5.7 Hz), 4.29 (2H, q, J=7.1 Hz), 4.47 (1H, d, J=5.5 Hz), 4.65–4.75 (1H, m), 6.31 (1H, d, J=8.2 Hz), 6.71 (2H, d, J=8.4 Hz), 6.90–7.00 (1H, m), 7.07 (2H, d, J=8.4 Hz), 7.44 (1H, d, J=1.8 Hz) Specific Rotation: [α]$_D^{29}$=−6.1° (c=0.56, Methanol)

2-[[2,6-Dichloro-4-[2-[[(1S, 2R)-2-hydroxy-2-(4-hydroxyphenyl)-1-methylethyl]amino]ethyl]phenyl] amino]-N, N-dimethylacetamide hydrochloride (Compound 16)

$^1$H-NMR (DMSO-d$_6$) δ ppm: 0.95 (3H, d, J=6.7 Hz), 2.85–3.00 (8H, m), 3.10–3.40 (3H, m), 4.14 (2H, s), 5.04 (1H, br s), 5.95 (1H, br), 6.76 (2H, d, J=8.6 Hz), 7.16 (2H, d, J=8.6 Hz), 7.29 (2H, s), 8.70 (2H, br), 9.40 (1H, br) Specific Rotation: [α]$_D^{31}$=−5.3° (c=0.60, Methanol)

EXAMPLE 4

N-[2,6-Dichloro-4-[2-[[(1S, 2R)-2-hydroxy-2-(4-hydroxyphenyl)-1-methylethyl]amino]ethyl]phenyl] aminoacetic acid (Compound 17)

Ethyl N-[2,6-dichloro-4-[2-[[(1S, 2R)-2-hydroxy-2-(4-hydroxyphenyl)-1-methylethyl]amino]ethyl]phenyl] aminoacetate (500 mg) was dissolved in 1N aqueous sodium hydroxide solution (5.0 ml), and the solution was stirred for 1 hour at room temperature. To the reaction mixture was added 1N hydrochloric acid (5.0 ml) under ice-cooling with stirring, and collection of the resulting precipitates by filtration gave N-[2,6-dichloro-4-[2-[[(1S, 2R)-2-hydroxy-2-(4-hydroxyphenyl)-1-methylethyl]amino]ethyl]phenyl]-aminoacetic acid (464 mg).

$^1$H-NMR (DMSO-d$_6$) δ ppm: 0.90 (3H, d, J=6.6 Hz), 2.65–2.80 (2H, m), 2.95–3.20 (3H, m), 3.76 (2H, s), 4.93 (1H, br s), 5.55 (1H, br), 6.72 (2H, d, J=8.5 Hz), 7.13 (2H, d, J=8.5 Hz), 7.16 (2H, s) Specific Rotation: [α]$_D^{30}$=−3.5° (c=1.00, Acetic acid)

EXAMPLE 5

The following compounds were prepared according to a similar manner to that described in Example 4 using the corresponding ester derivative.

N-[4-[2-[[(1S, 2R)-2-hydroxy-2-(4-hydroxyphenyl)-1-methylethyl]-amino]ethyl]phenyl]aminoacetic acid (Compound 18)

$^1$H-NMR (DMSO-d$_6$) δ ppm: 0.87 (3H, d, J=6.4Hz), 2.50–3.20 (5H, m), 3.51 (2H, s), 4.86 (1H, br s), 6.45 (2H, d, J=8.1 Hz), 6.70 (2H, d, J=8.4 Hz), 6.83 (2H, d, J=8.1 Hz), 7.11 (2H, d, J=8.4 Hz) Specific Rotation: [α]$_D^{25}$=−6.7° (c=0.75, Acetic acid)

4-[[2,6-Dichloro-4-[2-[[(1S, 2R)-2-hydroxy-2-(4-hydroxyphenyl)-1-methylethyl]amino]ethyl]phenyl] amino]butyric acid (Compound 19)

$^1$H-NMR (DMSO-d$_6$) δ ppm: 0.83 (3H, d, J=6.4 Hz), 1.60–1.75 (2H, m), 2.19 (2H, t, J=7.4 Hz), 2.45–2.85 (5H, m), 3.22 (2H, t, J=6.9 Hz), 4.40–4.60 (2H, m), 6.66 (2H, d, J=8.5 Hz), 7.04 (2H, d, J=8.5 Hz), 7.16 (2H, s) Specific Rotation: [α]$_D^{25}$=−3.3° (c=0.60, Acetic acid)

N-[2-Chloro-4-[2-[[(1S, 2R)-2-hydroxy-2-(4-hydroxyphenyl)-1-methylethyl]amino]ethyl]phenyl] aminoacetic acid (Compound 20)

$^1$H-NMR (DMSO-d$_6$) δ ppm: 0.90 (3H, d, J=6.4 Hz), 2.60–2.80 (2H, m), 2.90–3.20 (3H, m), 3.52 (2H, s), 4.95 (1H, br s), 5.35 (1H, br), 6.46 (1H, d, J=8.4 Hz), 6.72 (2H, d, J=8.6 Hz), 6.91 (1H, dd, J=8.4, 1.8 Hz), 7.05–7.20 (3H, m) Specific Rotation: [α]$_D^{30}$=−6.7° (c=1.00, Acetic acid)

N-[4-[2-[[(1S, 2R)-2-Hydroxy-2-(4-hydroxyphenyl)-1-methylethyl]-amino]ethyl]phenyl]-N-methylaminoacetic acid (Compound 21)

$^1$H-NMR (CD$_3$OD) δ ppm: 1.07 (3H, d, J=6.7 Hz), 2.84 (2H, t, J=8.1 Hz), 3.03 (3H, s), 3.10–3.25 (2H, m), 3.30–3.40 (1H, m), 3.86 (2H, s), 4.99 (1H, d, J=3.4 Hz), 6.64 (2H, d, J=8.8 Hz), 6.78 (2H, d, J=8.6 Hz), 7.02 (2H, d, J=8.8 Hz), 7.17 (2H, d, J=8.6 Hz) Specific Rotation: [α]$_D^{25}$=−6.9° (c=0.96, Acetic acid)

N-[2,6-Dichloro-4-[2-[[(1S, 2R)-2-hydroxy-2-(4-hydroxyphenyl)-1-methylethyl]amino]ethyl]phenyl]-N-methylaminoacetic acid (Compound 22)

$^1$H-NMR (DMSO-d$_6$) δ ppm: 0.84 (3H, d, J=6.6 Hz), 2.30–2.95 (8H, m), 3.76 (2H, s), 4.64 (1H, br s), 6.69 (2H, d, J=8.5 Hz), 7.09 (2H, d, J=8.5 Hz), 7.22 (2H, s) Specific Rotation: [α]$_D^{32}$=−5.9° (c=0.54, Methanol)

N-[2-Chloro-4-[2-[[(1S, 2R)-2-hydroxy-2-(4-hydroxyphenyl)-1-methylethyl]amino]ethyl]phenyl]-N-methylaminoacetic acid (Compound 23)

$^1$H-NMR (DMSO-d$_6$) δ ppm: 0.87 (3H, d, J=6.4 Hz), 2.65–2.90 (5H, m), 2.89 (3H, s), 3.60–3.70 (2H, m), 4.56 (1H, br), 6.65 (2H, d, J=8.5 Hz), 6.81 (1H, dd, J=8.3, 1.9 Hz), 6.95–7.05 (4H, m) Specific Rotation: [α]$_D^{25}$=−4.5° (c=0.75, Acetic acid)

N-[2,3-Dichloro-4-[2-[[(1S, 2 g)-2-hydroxy-2-(4-hydroxyphenyl)-1-methylethyl]amino]ethyl]phenyl] aminoacetic acid (Compound 24)

$^1$H-NMR (DMSO-d$_6$) δ ppm: 0.89 (3H, d, J=6.5 Hz), 2.75–3.25 (5H, m), 3.53 (2H, s), 4.90 (1H, br s), 5.62 (1H, br s), 6.45 (1H, d, J=8.5 Hz), 6.71 (2H, d, J=8.4 Hz), 7.01 (1H, d, J=8.5 Hz), 7.13 (2H, d, J=8.4 Hz) Specific Rotation: $[\alpha]_D^{25}$=−4.3° (c=0.47, Acetic acid)

N-[2,5-Dichloro-4-[2-[[(1S, 2R)-2-hydroxy-2-(4-hydroxyphenyl)-1-methylethyl]amino]ethyl]phenyl] aminoacetic acid (Compound 25)

$^1$H-NMR (DMSO-d$_6$) δ ppm: 0.89 (3H, d, J=6.5 Hz), 2.65–3.25 (5H, m), 3.55 (2H, s), 4.93 (1H, br s), 5.58 (1H, br s), 6.53 (1H, s), 6.71 (2H, d, J=8.4 Hz), 7.13 (2H, d, J=8.4 Hz), 7.19 (1H, s), 9.30 (1H, br) Specific Rotation: $[\alpha]_D^{25}$=−3.4° (c=0.83, Acetic acid)

N-[2,3,6-Trichloro-4-[2-[[(1S, 2R)-2-hydroxy-2-(4-hydroxyphenyl)-1-methylethyl]amino]ethyl]phenyl] aminoacetic acid (Compound 26)

$^1$H-NMR (DMSO-d$_6$) δ ppm: 0.89 (3H, d, J=6.4 Hz), 2.75–3.20 (5H, m), 3.70–3.90 (2H, m), 4.92 (1H, br s), 5.72 (1H, br), 6.71 (2H, d, J=8.4 Hz), 7.13 (2H, d, J=8.4 Hz), 7.25 (1H, s), 9.25 (1H, br) Specific Rotation: $[\alpha]_D^{25}$=−2.0° (c=0.60, Acetic acid)

N-[4-[2-[[(1S, 2R)-2-Hydroxy-2-(4-hydroxyphenyl)-1-methylethyl]-amino]ethyl]-2,5-dimethylphenyl] aminoacetic acid (Compound 27)

$^1$H-NMR (DMSO-d$_6$) δ ppm: 0.95 (3H, d, J=6.7 Hz), 2.05 (3H, s), 2.19 (3H, s), 2.75–3.10 (4H, m), 3.20–3.40 (1H, m), 3.77 (2H, s), 5.02 (1H, br s), 6.21 (1H, s), 6.65–6.85 (3H, m), 7.16 (2H, d, J=8.5 Hz), 9.40 (2H, br) Specific Rotation: $[\alpha]_D^{32}$=−6.9° (c=0.29, Methanol)

N-[2-Bromo-4-[2-[[(1S, 2R)-2-hydroxy-2-(4-hydroxyphenyl)-1-methylethyl]amino]ethyl]phenyl] aminoacetic acid (Compound 28)

$^1$H-NMR (DMSO-d$_6$) δ ppm: 0.92 (3H, d, J=6.5 Hz), 2.70–2.90 (2H, m), 3.00–3.40 (3H, m), 3.75 (2H, s), 4.93 (1H, br s), 5.36 (1H, br), 6.50 (1H, d, J=8.3 Hz), 6.74 (1H, d, J=8.5 Hz), 7.04 (1H, dd, J=8.3, 1.8 Hz), 7.14 (2H, d, J=8.5 Hz), 7.34 (1H, d, J=1.8 Hz) Specific Rotation: $[\alpha]_D^{27}$=−4.7° (c=0.51, Acetic acid)

N-[2,6-Dibromo-4-[2-[[(1S, 2R)-2-hydroxy-2-(4-hydroxyphenyl)-1-methylethyl]amino]ethyl]phenyl] aminoacetic acid (Compound 29)

$^1$H-NMR (DMSO-d$_6$) δ ppm: 0.89 (3H, d, J=6.6 Hz), 2.65–3.20 (5H, m), 3.75 (2H, s), 4.75–4.90 (1H, m), 5.40 (1H, br), 6.71 (2H, d, J=8.3 Hz), 7.11 (2H, d, J=8.3 Hz), 7.38 (2H, s) Specific Rotation: $[\alpha]_D^{29}$=−3.4° (c=1.29, Acetic acid)

N-[4-[2-[[(1S, 2R)-2-Hydroxy-2-(4-hydroxyphenyl)-1-methylethyl]amino]ethyl]-2-iodophenyl] aminoacetic acid (Compound 30)

$^1$H-NMR (DMSO-d$_6$) δ ppm: 0.92 (3H, d, J=6.6 Hz), 2.70–2.80 (2H, m), 3.00–3.25 (3H, m), 3.68 (2H, s), 4.93 (1H, br s), 5.15 (1H, br), 6.39 (1H, d, J=8.3 Hz), 6.73 (2H, d, J=8.6 Hz), 7.00–7.10 (1H, m), 7.14 (2H, d, J=8.6 Hz), 7.53 (1H, d, J=1.8 Hz) Specific Rotation: $[\alpha]_D^{27}$=−4.7° (c=0.51, Acetic acid)

EXAMPLE 6

2-[[2,6-Dichloro-4-[2-[[(1S, 2R)-2-hydroxy-2-(4-hydroxyphenyl)-1-methylethyl]amino]ethyl]phenyl] amino]-N-(2-methoxyethyl)-acetamide (Compound 31)

Ethyl N-[2,6-dichloro-4-[2-[[(1S, 2R)-2-hydroxy-2-(4-hydroxyphenyl)-1-methylethyl]amino]ethyl]phenyl] aminoacetate (44.3 mg) was dissolved in 2-methoxyethylamine (886 μl), and the solution was stirred for 48 hours at 80° C. The reaction mixture was concentrated in vacuo, and purification of the residue by medium pressure liquid column chromatography on aminopropyl silica gel (eluent: dichloromethane/methanol=10/1) gave 2-[[2,6-dichloro-4-[2-[[(1S, 2R)-2-hydroxy-2-(4-hydroxyphenyl)-1-methylethyl]amino]ethyl]phenyl]amino]-N-(2-methoxyethyl)-acetamide (27.7 mg).

$^1$H-NMR (DMSO-d$_6$) δ ppm : 0.80 (3H, d, J=6.4 Hz), 1.15–1.35 (1H, m), 2.40–2.80 (5H, m), 3.15–3.40 (7H, m), 3.86 (2H, d, J=5.7 Hz), 4.35–4.45 (1H, m), 4.85 (1H, d, J=3.9 Hz), 5.25 (1H, t, J=5.7 Hz), 6.67 (2H, d, J=8.5 Hz), 7.06 (2H, d, J=8.5 Hz), 7.16 (2H, s), 8.05–8.15 (1H, m), 9.15 (1H, br)

EXAMPLE 7

4-[2-[[2,6-Dichloro-4-[2-[[(1S, 2R)-2-hydroxy-2-(4-hydroxy-phenyl)-1-methylethyl]amino]ethyl]phenyl] amino]acetyl]morpholine (Compound 32)

4-[2-[[2,6-Dichloro-4-[2-[[(1S, 2R)-2-hydroxy-2-(4-hydroxyphenyl)-1-methylethyl]amino]ethyl]phenyl]amino] acetyl]-morpholine was prepared according to a similar manner to that described in Example 6 using morpholine instead of 2-methoxyethylamine.

$^1$H-NMR (CDCl$_3$) δ ppm: 0.96 (3H, d, J=6.4 Hz), 2.55–3.00 (6H, m), 3.40–3.45 (2H, m), 3.65–3.80 (7H, m), 4.17 (2H, d, J=4.9 Hz), 4.47 (1H, d, J=5.4 Hz), 5.40–5.50 (1H, m), 6.74 (2H, d, J=8.5 Hz), 6.98 (2H, s), 7.08 (2H, d, J=8.5 Hz) Specific Rotation: $[\alpha]_D^{30}$=+4.4° (c=1.01, DMSO)

Test Example 1

The experiment for measuring β$_3$-adrenoceptor stimulating effects

Urinary bladders of male ferrets (1100 to 1400 g in body weight) were isolated and urinary bladder smooth muscle strips of approximately 10 mm in length and approximately 2 mm in width were prepared. The experiment was conducted according to the Magnus method. The preparations with a tension of 1 g were exposed to Krebs-Henseleit solution maintained at 37° C. and gassed with a mixture of 95% oxygen and 5% carbon dioxide. Basal tensions of urinary bladder were measured isometrically with a force-displacement transducer and recorded on a rectigram. The drug was added cumulatively to the Magnus bath every 5 minutes. The drug efficacy was evaluated as the molar concentration of the drug required to produce 50% of the relaxation of urinary bladder smooth muscle before the addition of the drug (i.e., EC$_{50}$ value). In this experiment, tension of urinary bladder smooth muscle before the addition of the drug was expressed as 100% and tension of maximal relaxation after the addition of 10$^{-5}$ molar concentration of forskolin was expressed as 0%. The result was shown in the following Table 1.

TABLE 1

| Compound No. | EC$_{50}$(M) |
| --- | --- |
| 2 | 4.9 × 10$^{-8}$ |
| 16 | 1.3 × 10$^{-7}$ |
| 17 | 1.9 × 10$^{-8}$ |
| 18 | 2.4 × 10$^{-8}$ |
| 20 | 9.3 × 10$^{-10}$ |
| 21 | 5.2 × 10$^{-8}$ |
| 29 | 8.1 × 10$^{-8}$ |

TABLE 1-continued

| Compound No. | $EC_{50}(M)$ |
|---|---|
| 32 | $7.9 \times 10^{-8}$ |
| BRL-37344 | $1.6 \times 10^{-9}$ |

Test Example 2

The experiment for measuring $\beta_1$-adrenoceptor stimulating effects

Atria of male SD rats (250 to 400 g in body weight) were isolated and the experiment was conducted according to the Magnus method. The preparations with a tension of 0.5 g were exposed to Krebs-Henseleit solution maintained at 37° C. and gassed with a mixture of 95% oxygen and 5% carbon dioxide. The cardiac contractility was measured isometrically with a force-displacement transducer, and heart rate was recorded on a rectigram via a tachometer, and the drug was added cumulatively. The drug efficacy was evaluated as the molar concentration of the drug required to produce 50% increase of heart rate per minute (i.e., $EC_{50}$ value). In this experiment, increase of heart rate per minute after addition of $10^{-8}$ molar concentration of isoproterenol was expressed as 100%. The result was shown in the following Table 2.

TABLE 2

| Compound No. | $EC_{50}(M)$ |
|---|---|
| 2 | $5.0 \times 10^{-8}$ |
| 16 | $>10^{-4}$ |
| 17 | $>10^{-4}$ |
| 18 | $8.3 \times 10^{-8}$ |
| 20 | $2.3 \times 10^{-5}$ |
| 21 | $3.4 \times 10^{-5}$ |
| 29 | $>10^{-4}$ |
| 32 | $>10^{-4}$ |
| BRL-37344 | $2.7 \times 10^{-7}$ |

Test Example 3

The experiment for measuring $\beta_2$-adrenoceptor stimulating effects

Uteri of pregnant SD rats (pregnancy day 21) were isolated and longitudinal uterine muscle strips of approximately 15 mm in length and approximately 5 mm in width free from the basal plate were prepared. The experiment was conducted according to the Magnus method. The preparations with a tension of 0.5 g were exposed to Locke-Ringer solution maintained at 37° C. and gassed with a mixture of 95% oxygen and 5% carbon dioxide. Spontaneous contractions of myometrium were measured isometrically with a force-displacement transducer and recorded on a rectigram. The drug was added cumulatively to the Magnus bath every 5 minutes. The drug efficacy was evaluated as the molar concentration of the drug required to produce 50% of the inhibition of uterine contraction (i.e., $EC_{50}$ value) by comparing the total degree of uterine contraction during 5 minutes before the addition of the drug (100%) with the total degree of uterine contraction during 5 minutes after the addition of the drug. The result was shown in the following Table 3.

TABLE 3

| Compound No. | $EC_{50}(M)$ |
|---|---|
| 2 | $6.5 \times 10^{-7}$ |
| 17 | $1.4 \times 10^{-5}$ |
| 18 | $6.5 \times 10^{-7}$ |
| 20 | $3.3 \times 10^{-6}$ |
| 21 | $1.6 \times 10^{-6}$ |
| 32 | $1.7 \times 10^{-6}$ |
| BRL-37344 | $9.0 \times 10^{-9}$ |

Test Example 4

Acute toxicity test

To male ICR rats of 4 weeks age was administered intravenously N-[2,6-dichloro-4-[2-[[(1S, 2R)-2-hydroxy-2-(4-hydroxyphenyl)-1-methylethyl]amino]ethyl]phenyl]aminoacetic acid at a dose of 250 mg/kg. No death of animals was observed during 24 hours after the administration.

Industrial Applicability

The phenylaminoalkylcarboxylic acid derivative represented by the above general formula (I) and pharmaceutically acceptable salts thereof of the present invention have excellent $\beta_3$-adronoceptor stimulating effects and are extremely useful as medicaments such as agents for the prevention or treatment of obesity, hyperglycemia, the diseases caused by intestinal hypermotility, pollakiuria, urinary incontinence, depression, or the diseases caused by biliary calculi or hypermotility of biliary tract.

What is claimed is:

1. A phenylaminoalkylcarboxylic acid derivative represented by the general formula:

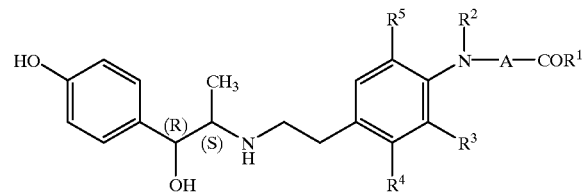

(wherein $R^1$ represents a hydroxy group, a lower alkoxy group, an aralkoxy group, an amino group, an alicyclic amino group or a mono or di(lower alkyl)amino group which may have a hydroxy group or a lower alkoxy group as a substituent; $R^2$ represents a hydrogen atom or a lower alkyl group; $R^3$ represents a hydrogen atom or a halogen atom; $R^4$ and $R^5$ are the same or different and each represents a hydrogen atom, a halogen atom or a lower alkyl group; A represents a lower alkylene group; the carbon atom marked with (R) represents a carbon atom in (R) configuration; and the carbon atom marked with (S) represents a carbon atom in (S) configuration) or a pharmaceutically acceptable salt thereof.

2. A phenylaminoalkylcarboxylic acid derivative as claimed in claim 1, represented by the general formula:

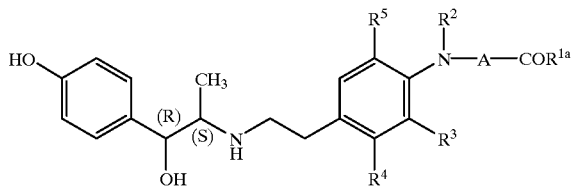

(wherein $R^{1a}$ represents a hydroxy group or a lower alkoxy group; $R^2$ represents a hydrogen atom or a lower alkyl group; $R^3$ represents a hydrogen atom or a halogen atom; $R^4$ and $R^5$ are the same or different and each represents a hydrogen atom, a halogen atom or a lower alkyl group; A represents a lower alkylene group; the carbon atom marked with (R) represents a carbon atom in (R) configuration; and the carbon atom marked with (S) represents a carbon atom in (S) configuration) or a pharmaceutically acceptable salt thereof.

3. A phenylaminoalkylcarboxylic acid derivative as claimed in claim 1, represented by the general formula:

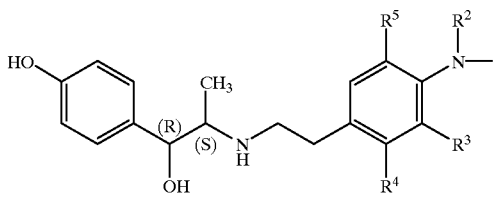

(wherein $R^1$ represents a hydroxy group, a lower alkoxy group, an aralkoxy group, an amino group, an alicyclic amino group or a mono or di(lower alkyl)amino group which may have a hydroxy group or a lower alkoxy group as a substituent; $R^2$ represents a hydrogen atom or a lower alkyl group; $R^3$, $R^{4a}$ and $R^{5a}$ are the same or different and each represents a hydrogen atom or a halogen atom; A represents a lower alkylene group; the carbon atom marked with (R) represents a carbon atom in (R) configuration; and the carbon atom marked with (S) represents a carbon atom in (S) configuration) or a pharmaceutically acceptable salt thereof.

4. A phenylaminoalkylcarboxylic acid derivative as claimed in claim 2, represented by the general formula:

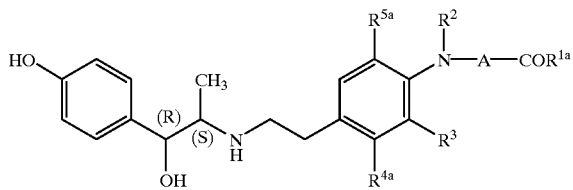

(wherein $R^{1a}$ represents a hydroxy group or a lower alkoxy group; $R^2$ represents a hydrogen atom or a lower alkyl group; $R^3$, $R^{4a}$ and $R^{5a}$ are the same or different and each represents a hydrogen atom or a halogen atom; A represents a lower alkylene group; the carbon atom marked with (R) represents a carbon atom in (R) configuration; and the carbon atom marked with (S) represents a carbon atom in (S) configuration) or a pharmaceutically acceptable salt thereof.

5. A phenylaminoalkylcarboxylic acid derivative as claimed in claim 4, represented by the general formula:

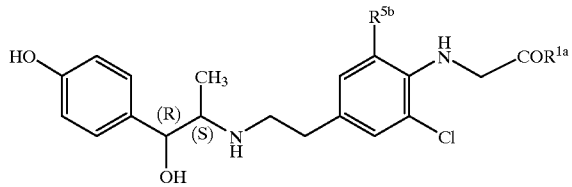

(wherein $R^{1a}$ represents a hydroxy group or a lower alkoxy group; $R^{5b}$ represents a hydrogen atom or a chlorine atom; the carbon atom marked with (R) represents a carbon atom in (R) configuration; and the carbon atom marked with (S) represents a carbon atom in (S) configuration) or a pharmaceutically acceptable salt thereof.

6. A pharmaceutical composition comprising a phenylamino-alkylcarboxylic acid derivative or a pharmaceutically acceptable salt thereof as claimed in claim 1, 2, 3, 4 and 5.

7. A $\beta_3$-adrenoceptor stimulant comprising as the active ingredient a phenylaminoalkylcarboxylic acid derivative or a pharmaceutically acceptable salt thereof as claimed in claim 1, 2, 3, 4, 5.

8. An agent for the prevention or treatment of obesity, hyperglycemia, the diseases caused by intestinal hypermotility, pollakiuria, urinary incontinence, depression, or the diseases caused by biliary calculi or hypermotility of biliary tract which comprises as the active ingredient a phenylaminoalkylcarboxylic acid derivative or a pharmaceutically acceptable salt thereof as claimed in claim 1, 2, 3, 4, 5.

9. A method for the prevention or treatment of obesity, hyperglycemia, the diseases caused by intestinal hypermotility, pollakiuria, urinary incontinence, depression, or the diseases caused by biliary calculi or hypermotility of biliary tract which comprises administrating a therapeutically effective amount of a phenylaminoalkylcarboxylic acid derivative or a pharmaceutically acceptable salt thereof as claimed in claim 1, 2, 3, 4, 5.

* * * * *